United States Patent [19]

Revell et al.

[11] Patent Number: 5,962,392
[45] Date of Patent: Oct. 5, 1999

[54] THICKENED PERACID COMPOSITIONS

[75] Inventors: Christopher Revell, Warrington; Enid Margaret Ellis, Widnes, both of United Kingdom

[73] Assignee: Solvay Interox Limited, United Kingdom

[21] Appl. No.: 08/860,228

[22] PCT Filed: Dec. 8, 1995

[86] PCT No.: PCT/EB95/02866

§ 371 Date: Jun. 23, 1997

§ 102(e) Date: Jun. 23, 1997

[87] PCT Pub. No.: WO96/19559

PCT Pub. Date: Jun. 27, 1996

[30] Foreign Application Priority Data

Dec. 21, 1994 [GB] United Kingdom ............... 9425881

[51] Int. Cl.$^6$ ................ C11D 7/18; C11D 3/395
[52] U.S. Cl. ............... 510/372; 510/373; 510/191; 510/218; 510/238; 510/503; 134/3; 422/28; 252/186.23; 252/186.26; 252/186.42
[58] Field of Search .............. 252/186.23, 186.26, 252/186.42; 510/310, 372, 373, 191, 218, 238, 503; 514/557; 134/3; 422/28

[56] References Cited

U.S. PATENT DOCUMENTS

| | | | |
|---|---|---|---|
| 4,585,570 | 4/1986 | Nelson | 510/503 |
| 4,652,198 | 3/1987 | Humphreys et al. | 252/186.23 |
| 4,828,747 | 5/1989 | Rerek et al. | 252/186.26 |
| 4,929,377 | 5/1990 | Emmons et al. | 252/186.26 |
| 5,314,636 | 5/1994 | Rek et al. | 510/310 |
| 5,391,324 | 2/1995 | Reinhardt et al. | 252/186.42 |
| 5,425,898 | 6/1995 | Phillippi et al. | 252/186.26 |
| 5,451,346 | 9/1995 | Amou et al. | 252/186.23 |
| 5,489,706 | 2/1996 | Revell | 562/3 |
| 5,656,580 | 8/1997 | Carrie et al. | 510/191 |
| 5,851,979 | 12/1998 | Scialli et al. | 510/372 |

FOREIGN PATENT DOCUMENTS

| | | |
|---|---|---|
| 0 201 958 | 11/1986 | European Pat. Off. |
| 0 442 549 | 8/1991 | European Pat. Off. |
| 0 779 357 | 6/1997 | European Pat. Off. |
| WO 9219287 | 11/1992 | WIPO |

*Primary Examiner*—Richard D. Lovering
*Assistant Examiner*—Daniel S. Metzmaier
*Attorney, Agent, or Firm*—Larson & Taylor

[57] ABSTRACT

Thickened aqueous compositions comprising soluble peracids, particularly peracetic acid are provided. The compositions are thickened by the use of one or more aliphatic alcohol ethoxylates having the general formula: $R^1R^2CH-(OCH_2CH_2)_n-OH$ in which $R^1$ and $R^2$ are each either hydrogen or linear or branched alkyl such that $R^1$ plus $R^2$ has a total of from 7 to 22 carbon atoms, and n is selected in the range of 1 to 15, such that the number ratio of carbon atoms in $R^1$ plus $R^2$:n is greater than or equal to 3:1; and a co-surfactant selected from the group consisting of anionic surfactants, amine oxides, amphoteric surfactants and quaternary ammonium compounds.

33 Claims, No Drawings

THICKENED PERACID COMPOSITIONS

FIELD OF THE INVENTION

This application is filed under 35 U.S.C. §371 based on PCT/EP95/02866, filed Dec. 8, 1995.

The present invention relates to thickened compositions and particularly to thickened peracid compositions.

BACKGROUND OF THE INVENTION

During recent years, increasing attention has been paid by industry and the general public in Western Europe and North America to the environmental effects of the many substances that are employed in modern life. One of the classes of substances which have hitherto been widely employed comprises chlorine and oxychlorine derivatives thereof. Such compounds have been reported to generate under appropriate circumstances carcinogenic compounds and as a result, industry is seeking alternatives or replacements for such compounds in order to allay any residual public anxiety.

An alternative class of compounds comprises peroxygen compounds, of which one sub-class of especial interest comprises peracids which contain the moiety —CO—OOH. Peracids, like hydrogen peroxide, enjoy the substantial advantage of generating oxygen, either as such or in an active form during its deployment rather than chlorine or active chlorine species upon which environmentalists currently cast doubts. Furthermore, for a range of purposes such as disinfection, oxidation and bleaching, many of which are encountered domestically, peracids are more effective in general than hydrogen peroxide.

A number of the peracids are either liquid themselves or are produced conveniently in aqueous solution. Although such compositions are particularly appropriate for the treatment of or incorporation in liquid media, they are less appropriate for the treatment of solid surfaces, and particularly non-horizontal surfaces on account of the ability of liquid compositions to flow away from the point of contact. In consequence, and in order to extend the range of applications for peracids, it would be desirable to devise peracid-containing compositions that flowed less freely.

In principle, liquid compositions can be rendered less free-flowing by the incorporation of materials which thicken the liquid or introduce structure intothe liquid. However, substances which have hitherto been effective thickeners for other liquids cannot be presumed automatically to be suitable for thickening liquid peracids or peracid solutions. This difficulty derives from the very same properties of the peracids that make them effective oxidising agents and bleaches. Interaction with thickeners during storage can result in the mutual decomposition of the peracid and the thickener, which in turn not only negates the beneficial effects of thickening, but also progressively removes the capability of the peracid to perform its desired task. It will be recognised that the problem is especially apparent in the case of peracids which are themselves either liquid or are present in solution. There is also a second important difficulty in attempting to thicken peracid solutions. The presence of the peracid and the corresponding carboxylic acid from which it can be derived, tends to significantly inhibit thickening. It is believed that the difficulty arises from interference of the peracid and/or carboxylic acid with aqueous structuring mechanisms which enable surfactants and like materials to thicken aqueous solutions. However, it will be understood that the instant invention does not depend upon the accuracy of the foregoing belief or explanation, but instead it relies upon the results actually demonstrated.

By comparison with soluble peracids, the problem can be somewhat diminished in the case of substantially insoluble solid peracids that are suspended in particulate form in aqueous media, because the peracid and the liquid constitute different physical phases that consequently minimise the extent of chemical interaction between them, and the thickening of the aqueous phase can occur with a lessened risk of interference from dissolved peracid species. European patent application No. 0 160 342 discloses that insoluble peracids can be suspended by the use of a combination of a $C_{12}$–$C_{15}$, primary alcohol ethoxylate having 7 ethylene oxides, alkylbenzene sulphonate and very high levels (>6% w/w) of an electrolyte such as sodium sulphate. European patent application No. 0 201 958 teaches that insoluble peracids can be suspended by a $C_{12}$–$C_{14}$ alcohol ethoxylate having 7.5 ethoxylates in combination with sodium dodecylbenzene sulphonate, but that the pH of these compositions must be maintained between 3.5 and 4.1, a very narrow and restrictive pH range. European patent application No. 0 442 549 teaches that insoluble peracids can be suspended by $C_{12}$–$C_{15}$ alcohol ethoxylate having 3 ethoxylates in combination with a secondary alkane sulphonate and 10% w/w sodium sulphate.

It will be understood that some other potential thickeners may initially or after a brief period of storage produce a much thickened composition, but one which is rather unstable, in that its viscosity falls away rapidly from its peak. Tests employing anionic polyacrylamides fell into that category.

It will be recognised that many applications for thickened peroxygens result in the thickened compositions being discharged into the waste water system, and therefore it is desirable that the thickeners employed should possess an acceptable degree of biodegradability, and preferably the more biodegradable the thickener the better. UK patent application No. 2,255,507 discloses that a combination of a dinonylphenol ethoxylate with an amine oxide or a mixture of a fatty alcohol ethoxylate and a polyether can be employed to thicken peracetic acid solutions. However, dinonyl phenol ethoxylates are very poorly biodegradable, and are not acceptable for discharge into drainage water in many countries. The peracetic acid compositions thickened with dinonylphenolethoxylates were also found to develop a strong yellow colouration on storage, which may be unacceptable in certain potential applications.

International patent application No. WO/9424863 discloses that certain block copolymers can be employed to thicken peracetic acid solutions in which the concentration of peracetic acid is restricted to less than 0.09% by weight. The concentration of peracid in such solutions is very low, and is unsuitable for use in applications where higher concentrations of peracetic acid are required or desired.

It is an object of the present invention to seek to identify further thickening substances which are capable of thickening aqueous compositions comprising a water soluble peracid. It is a second object of some embodiments to identify further materials capable of thickening aqueous compositions comprising a water soluble peracid and obtain thereby compositions which are relatively stable chemically and physically during storage. It is a third object of a certain embodiments of the present invention to identify further materials which can thicken aqueous compositions comprising a water soluble peracid to produce viscous compositions which can be applied for disinfecting and/or cleansing purposes to non-horizontal surfaces. It is a fourth object of selected embodiments to seek to identify further thickening substances which are capable of thickening aqueous compositions comprising a water soluble peracid, and which have acceptable biodegradability. It is a fifth objective of particular embodiments of the present invention to identify a thickening system for aqueous compositions comprising a water soluble peracid which does not require the presence of high levels of electrolyte, and/or is not restricted to very dilute peracid concentrations.

SUMMARY OF THE INVENTION

According to a first aspect of the present invention there are provided thickened aqueous compositions comprising a soluble peracid in solution together with a thickener characterised in that the thickener comprises:

(a) one or more aliphatic alcohol ethoxylates having the general formula:

$$R^1R^2CH—(OCH_2CH_2)n—OH$$

in which $R^1$ and $R^2$ are each either hydrogen or linear or branched alkyl such that $R^1$ plus $R^2$ has a total of from 7 to 22 carbon atoms, and n is selected in the range of 1 to 15, such that the number ratio of carbon atoms in $R^1$ plus $R^2$:n is greater than or equal to 3:1 and (b) a co-surfactant selected from the group consisting of anionic surfactants, amine oxides, amphoteric surfactants and quaternary ammonium compounds in an amount sufficient to increase the viscosity of the composition.

According to a second aspect of the present invention, there is provided a process for thickening soluble peracid solutions, characterised in that it comprises introducing:

(a) one or more aliphatic alcohol ethoxylates having the general formula:

$$R^1R^2CH—(OCH_2CH_2)_n—OH$$

in which $R^1$ and $R^2$ are hydrogen or linear or branched alkyl such that $R^1$ plus $R^2$ has a total of from 7 to 22 carbon atoms, and n is selected in the range of 1 to 15, such that the number ratio of carbon atoms in $R^1$ plus $R^2$: n is greater than or equal to 3:1 and (b) a co-surfactant selected from the group consisting of anionic surfactants, amine oxides, amphoteric surfactants and quaternary ammonium compounds in an amount sufficient to increase the viscosity of the composition.

By the use of a thickening system of the present invention it is possible to obtain solutions which are thickened and in which the peracid compound decomposes by not more than an acceptable extent during storage. In other words, the composition enjoys both physical and chemical stability.

DETAILED DESCRIPTION OF THE INVENTION

Soluble peracids which can be thickened by the thickening system of the present invention include low molecular weight aliphatic peroxyacids, for example containing up to 6 carbon atoms, of which especially preferred examples comprise peracetic acid and perpropionic acid. Other examples include perbutyric acid, percitric acid, permalic acid, perglycolic acid perlactic acid, persuccinic acid, perglutaric acid and peradipic acid. Further examples include peracids derived from monoalkylesters, and preferably monomethyl esters, of diperacids, particularly monomethylperglutarate, monmethylperadipate and monomethylpersuccinate. The compositions may alternatively include soluble aromatic peroxyacids, such monoperphthalic acid, or sulphoperbenzoic acid. A mixture of two or more peracids, particularly a mixture of persuccinic, perglutaric and peradipic acids, may be employed, if desired.

The soluble peracid may be present in a wide range of concentrations, subject to the requirement of total amount of acid plus peracid discussed below, for example up to 40%, often up to 15% and more often up to 10%. For any component, % herein is by weight based on the total weight of the composition, unless specifically stated otherwise. The lower limit is at the discretion of the user, but is normally not below 0.01%. The invention is particularly applicable to ready to use compositions containing a low concentration of peracid, and for example compositions intended for application for cleansing and/or disinfecting purposes to hard surfaces and particularly to non-horizontal surfaces. Such dilute compositions typically contain not less than 0.05%, often not less than 0.1% and more often not less than 0.5%, and often not more than 5%, more often not more than 2% by weight of peracid. For example in a number of practical embodiments the peracid content will be from 0.2%, often from 0.6%, to 1.5% by weight. It will be recognised that such compositions may contain a significant concentration of hydrogen peroxide, which may, for example, comprise from 1 to 15% of the composition, and in a number of embodiments from 3 to 10%.

Peracid compositions suitable for use in the compositions according to the present invention, and particularly those containing aliphatic peracids, are often conveniently derived by oxidation of the corresponding aliphatic carboxylic acid with aqueous hydrogen peroxide, optionally in the presence of a strong acid catalyst, and will often contain residual amounts of both the carboxylic acid and hydrogen peroxide. The total amount of peracid plus corresponding carboxylic acid is less than 30% w/w, preferably less than 25% w/w and particularly preferably 16% w/w or less. The minimum water content is usually about 50% w/w, and the water content is often greater than 60% w/w, preferably greater than about 65%. Thus, the compositions may contain up to 40% of the corresponding carboxylic acid and up to 40% hydrogen peroxide, with a minimum water content usually of 20%. However, i. In dilute peracid solutions, the concentration of the carboxylic acid and of hydrogen peroxide each tend to be selected in the range from 0.1% to 12%. The total concentration of carboxylic acid plus percarboxylic acid is often from 0.3 to 15%. It is often convenient to restrict the concentration of hydrogen peroxide to no greater than 7%. In many preferred compositions, equilibrium amounts of carboxylic acid, percarboxylic acid and hydrogen peroxide are present.

The thickening system of the present invention comprises a combination of (a) a range of aliphatic alcohol ethoxylates and (b) a co-surfactant. The aliphatic alcohol ethoxylates (a) can be derived from either primary or secondary alcohols, and have the general formula:

$$R^1R^2CH—(OCH_2CH_2)_n—OH$$

in which $R^1$ and $R^2$ are hydrogen or linear or branched alkyl such that $R^1$ plus $R^2$ has a total of from 7 to 22 carbon atoms, and n is selected in the range of 1 to 15, such that the number ratio of carbon atoms in $R^1$ plus $R^2$:n is greater than or equal to 3:1.

When neither $R^1$ nor $R^2$ are a hydrogen atom, $R^1$ and $R^2$ preferably have in total from 10 to 18 carbon atoms, and the number ratio of carbon atoms in $R^1$ plus $R^2$:n is preferably in the range of from 4:1 to 7:1.

When either $R^1$ or $R^2$ is a hydrogen atom, the total number of carbon atoms is preferably from 7 to 16 carbon atoms, particularly preferably from 9 to 16 carbon atoms and the number ratio of carbon atoms in $R^1$ plus $R^2$:n is preferably in the range of from 4:1 to 9:1, particularly preferably from 5:1 to 8:1.

The amount of aliphatic alcohol ethoxylate thickener employed for a given extent of thickening is generally selected in accordance with the proportion of peracid plus carboxylic acid in the composition, although the ratio of thickener to total peracid plus acid is not necessarily linear. It is desirable to select the concentration of aliphatic alcohol ethoxylate to be not less than 2.5%, and usually not more than 15%, and in many instances thickening of dilute peracid compositions can be achieved with quite small amounts of aliphatic alcohol ethoxylate, such as from 3 to 10%.

The biodegradability of the alcohol ethoxylates of the present invention is often greater than 80% as measured by OECD test 301E and is considered acceptable in many countries for discharge into municipal effluents.

The co-surfactant (b) is selected from anionic, amine oxide, amphoteric and quaternary ammonium surfactants and mixtures thereof. The concentration of co-surfactant is normally selected to be not less than 0.1%, and often not less than 0.25%, and is normally not more than 5%, and often not more than 3%. To some extent, the amount selected depends upon the chemical nature of the co-surfactant.

Amine oxides that can be employed as co-surfactant (b) often contain from 14 to 24 carbons, including at least one long chain group, for example containing from 10 to 18 carbons and the remainder comprise short chain alkyl groups such as methyl, ethyl or propyl or hydroxyl substituted alkyl groups such as hydroxyethyl. The long chain alkyl group may be synthetically derived, or may be derived from natural products, for example coconut or tallow oil derivatives.

Anionic surfactants that can be employed as co-surfactant (b) include alkylsulphates and alkylbenzenesulphonates, which may be present either as the free acid or as an alkali metal or ammonium salt. Suitable alkylbenzenesulphonates include linear and branched alkylbenzenesulphonates, with linear alkylbenzenesulphonates being preferred. Preferably, the alkyl moiety comprises from 6 to 18 carbon atoms, and more preferably from 10 to 14 carbon atoms. The most preferred alkylbenzenesulphonate is dodecylbenzenesulphonate.

Suitable alkylsulphates include linear and branched alkylsulphates. Preferably, the alkyl moiety comprises from 6 to 18 carbon atoms, and more preferably from 8 to 14 carbon atoms. Examples of suitable alkylsulphates include sodium 2-ethylhexylsulphate and sodium laurylsulphate. A further suitable class of akylsulphates is alkyl ether sulphates wherein the sulphate group is bonded to the alkyl group via one or more, such as from 2 to 6, ethoxylate groups.

Amphoteric surfactants that can be employed as co-surfactant (b) are generally selected to be substantially free from chloride, bromide and iodide ions because such ions can react with and decompose peracids. Amphoteric surfactants can be selected from betaines, including fatty dimethyl betaines, fatty amidopropyldimethyl betaines, fatty bishydroxyethyl betaines and fatty dimethylsulphobetaines. In some cases, the amphoteric surfactants will be defined by the general chemical formula:

R—NR'—X where R represents an optionally substituted alkyl or aryl group, R' represents hydrogen or an optionally substituted alkyl or aryl group, and X is selected from one of the groups having the respective formulae:

 Formula (1)

where m is an integer and Y represents hydrogen or a monovalent cation such as sodium, potassium or ammonium, or

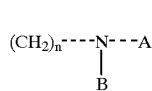 Formula (2)

where n is an integer, A represents a group having the formula: $[(CH_2)_p NR'']_q$—$(CH_2)_r CO_2 Y$ where p, q and r represent integers, R" represents hydrogen or an alkyl or aryl group, and Y represents hydrogen or a monovalent cation such as sodium, potassium or ammonium, and B represents hydrogen, an alkyl or aryl group or may have the same general formula as A. In certain embodiments, the amphoteric surfactant has the general formula where X corresponds to formula (2) above, q is zero and B has the same general formula as A.

In the amphoteric surfactants employed in many embodiments of the present invention, R often contains from about 6 to about 18 carbons, and especially from about 8 to about 14 carbons and in many instances comprises a linear group. R can be synthetically derived, or can be obtained from natural sources, for example, from tallow or from coconut oil. In one particular class of amphoterics, R is derived from imidazoline.

Quaternary ammonium surfactants that can be employed as co-surfactant (b) can be represented by the general formula $R^a R^b R^c R^d N^+ Q^-$ in which substituents $R^a$, $R^b$, $R^c$, and $R^d$ each represent an alkyl or aryl group or two of which combine with the nitrogen to form a heterocyclic nucleus, the total number of carbons in $R^a$ to $R^d$ normally comprising from about 10 to about 30 carbons, and Q represents a counterion, usually an anion which is not oxidised by peracids, such as hydroxyl, sulphate or alkyl sulphate, particularly methosulphate. One or two of the substituents normally contains from 8 to 18 linear carbons often from C12 to C16, or forms part of the heterocyclic nucleus such pyridinium. One of the substituents can conveniently comprise a benzyl group. The remaining substituents usually are selected from C1 to C4 alkyl groups, and especially methyl or ethyl. Preferred quaternary ammonium surfactants include alkyltrimethyl and alkylbenzyldimethyl ammonium salts.

In many embodiments of the present invention, the weight ratio of alcohol ethoxylate (a) to co-surfactant (b) is selected to be in the range of from 1:5 to 50:1, often from 1:2 to 30:1, and more often from 2:1 to 20:1. In certain embodiments of the present invention, good results have been achieved employing a weight ratio of alcohol ethoxylate (a) to co-surfactant (b) in the range of from 3:1 to 18:1, particularly from 4:1 to 15:1.

The co-surfactants of the present invention are often selected such that their biodegradability is considered acceptable in many countries for discharge into municipal effluents.

The thickened compositions according to the present invention usually have a viscosity of greater than 30 cPs, and more often greater than 50 cPs. By suitable choice of thickener system and the relative concentrations of the surfactants therein it is possible to obtain peracid compositions having a viscosity in the region of 100 to 500 cPs. Such compositions are advantageous in that they are sufficiently viscous to inhibit movement of thin layers adhering to non-horizontal surfaces, but are sufficiently fluid to enable them to be poured from bulk containers or to be ejected under pressure through nozzles. Generally, the higher the concentration of co-surfactant (b) and the higher the ratio of alcohol ethoxylate (a) co-surfactant (b), the higher will be the viscosity of the composition. In some embodiments of the present invention, particularly good results have been achieved with peracid compositions comprising up to a total of 15% w/w, especially 6% to 12% w/w, peracid plus corresponding acid, by employing a concentration of co-surfactant (b) of from 0.25 to 1.5%, and a ratio of alcohol ethoxylate (a) co-surfactant (b) of from 6:1 to 12:1.

It will be recognised that the viscosity of the compositions according to the present invention can be affected by factors such as the ionic strength of the composition and particularly when the peracid comprises an aliphatic peracid, by the concentration of peracid and corresponding aliphatic acid in the composition. As a general rule, the higher the ionic strength of the composition and/or the concentration of peracid and corresponding aliphatic acid, the higher the concentration of alcohol ethoxylate and/or co-surfactant will need to be employed to achieve a given viscosity. In certain preferred embodiments, the ionic strength of the composition is substantially completely derived from the peracid, for example, a peracid, hydrogen peroxide and acid equilibrium mixture, the thickening system, stabilisers for the peroxygen compound, and from the co-surfactant if this is ionic in nature.

A further factor which influences the viscosity of the compositions is the pH of the composition. The pH of compositions according to the present invention, including the peracids, alcohol ethoxylate and co-surfactant and any associated stabiliser for the peroxygen compound, is in many embodiments of the present invention selected to be 2.0 or more, and particularly where the peracid is an aliphatic peracid, commonly up to 5. In many embodiments of the present invention, good results have been achieved when the pH of the thickened composition has been in the range of from 2.3 to 4.0, and particularly 2.5 to 3.5. The pH of low pH compositions, such as equilibrium peracetic acid solutions where a mineral acid catalyst has been employed to accelerate the equilibration, and which may not be efficiently thickened by the thickening system according to the present invention, can be increased by the addition of suitable alkali to reach the desired pH, subject to the constraints placed upon the thickening system by the increase in ionic strength that such a pH adjustment involves. Preferably, the compositions according to the present invention are prepared by methods which avoid the use of concentrations of mineral acids that impair the efficiency of the thickening system. Particularly preferred are compositions substantially free from mineral acid.

The compositions may include one or more stabilisers for peracids and/or hydrogen peroxide so as to encourage the chemical stability of the thickened products. Known stabilisers for peroxygen compounds include aminopolycarboxylic acids, such as EDTA and DTPA, or N-heterocyclic aromatic carboxylic acids such as quinolinic acid, picolinic acid and dipicolinic acid. Particularly effective stabilisers comprise organic polyphosphonic acids, including hydroxyethylidene-diphosphonic acid and aminopolymethylene phosphonic acids. The latter often satisfy the general formula:

in which X represents $-CH_2-PO_3H_2$ R represents H or the two R substituents combine to complete a cyclohexane ring, and n is an integer from 1 to 3. Examples of the formula include ethylenediaminetetra-(methylene phosphonic acid), diethylenetriaminepenta-(methylene phosphonic acid) and cyclohexanediaminetetra-(methylene phosphonic acid). A combination of any two or more of the aforementioned types of stabiliser can be employed. The weight proportion of stabilisers in the invention compositions is often up to 2%.

In addition to the foregoing components, the composition may also contain one or more perfumes and/or dyes, preferably selected at least partly on the basis of resistance to oxidation.

According to one preferred aspect of the present invention, there is provided a thickened aqueous composition comprising peracetic acid in solution together with a thickener characterised in that the thickener comprises:

(a) an aliphatic alcohol ethoxylate having the general formula:

in which $R^1$ and $R^2$ are hydrogen or linear or branched alkyl such that $R^1$ plus $R^2$ has a total of from 7 to 22 carbon atoms, and n is selected in the range of 1 to 15, such that the number ratio of carbon atoms in $R^1$ plus $R^2$:n is greater than or equal to 3:1 and (b) an amine oxide or alkylbenzenesulphonate co-surfactant in an amount sufficient to increase the viscosity of the composition, and that the pH of the thickened composition is from 2.3 to 4.

According to another preferred aspect of the present invention, there is provided a thickened aqueous composition comprising peracetic acid in solution together with a thickener characterised in that the thickener comprises:

(a) an aliphatic alcohol ethoxylate having the general formula:

in which $R^1$ and $R^2$ are linear alkyl groups such that $R^1$ plus $R^2$ has a total of from 7 to 22 carbon atoms, and n is selected in the range of 1 to 5, such that the number ratio of carbon atoms in $R^1$ plus $R^2$:n is greater than or equal to 4:1 and (b) from 0.25% to 5% w/w of an amine oxide or alkyl-benzenesulphonate co-surfactant, and wherein the weight ratio of aliphatic alcohol ethoxylate to cosurfactant is from 4:1 to 15:1, and the pH of the thickened composition is from 2.3 to 4.

The compositions of the present invention can be made by introducing the selected amount of each component in the thickening system into the aqueous solution of peracid and any residual amounts of the corresponding carboxylic acid and hydrogen peroxide, and agitating the mixture to distribute the components substantially evenly through the mixture. This can be conducted at any convenient temperature, for example at the prevailing ambient temperature which is typically in the range of from 10 to 35° C. Alternatively, the mixture may be gently heated to not higher than 50° C. so as to encourage rapid distribution of the components and the mixture thereafter permitted to cool to ambient.

A preferred method of preparing the compositions according to the present invention is to prepare a pre-mix of the aliphatic alcohol ethoxylate (a) with the co-surfactant (b), prior to addition of the peracid solution to the pre-mix.

It will be recognised that the peracid compositions according to the present invention can be prepared by introducing a thickening system as herein described into a mixture of hydrogen peroxide and organic acid, and allowing peracid to form in situ. This in situ preparation is applicable to the methods described in the preceding two paragraphs, and is particularly applicable where there is likely to be a significant delay, such as 2 to 3 weeks or more, between preparation of the thickened composition and its use.

Some of the compositions of the present invention, and particularly those having a viscosity in the region of 100 to 500 cPs are intended for application domestically to surfaces, such as non-horizontal surfaces, which it is desired to disinfect and clean, thereby taking advantage of the disinfectant properties of the peroxygen compound, especially the peracid and the cleansing properties of the detergents. The peroxygen compositions when they have very high viscosities can be regarded as solids, and as such may be incorporated in particulate or granular washing or disinfecting compositions or dispersed in blocks or bars. Such blocks or bars may also incorporate substances such as waxes, either natural or synthetic polymers or very poorly soluble aliphatic carboxylic acids or poorly soluble derivatives and/or mixtures thereof which can regulate and retard the extent of contact between the peroxygen compound composition and for example a liquid medium such as flushing toilet water.

Accordingly, a further aspect of the present invention comprises the use the aforementioned invention compositions for disinfecting and cleansing by applying the composition to a hard surface and permitting contact to be maintained until at least some disinfection has occurred.

The invention compositions may be applied using conventional means and will also take into account the physical state of the composition, particularly whether it is a viscous pourable liquid or a gel. Thus, in its simplest, the compositions may be poured or smeared onto a distributor such as a cloth or sponge and applied to a receiving surface by passage of distributor across the surface. Alternatively, the compositions which have a sufficiently low viscosity for them to be pourable, may be forced through a distributing nozzle directly onto the receiving surface, for example by squeezing a resilient deformable storage container. Compositions in gel form may be applied by a spatula or like article or as indicated previously by incorporation in a host composition or block.

The surfaces onto which the compositions may be applied are often domestic and especially in the kitchen and other locations in which micro-organisms may be found. Suitable receptive surfaces are usually made from wood, glass, ceramics, plastic laminates and metal, and include work surfaces, sinks, pipework, walls, floors, and especially toilet bowls. It will be recognised, though, that similar potentially infected surfaces may be found in non-domestic situations, such as in commercial kitchens, food processing apparatus or containers or brewery or distillery vessels or hospitals or in animal or poultry-rearing establishments or in glass houses or other areas where the maintenance of hygienic conditions is important. The present invention includes the use of invention compositions in such non-domestic situations.

The compositions may subsequently be removed from the surfaces by water washing, possibly applied using a cloth, sponge or like article. Having described the invention in general terms, specific embodiments thereof will now be described in greater detail by way of example only.

EXAMPLE 1

In Example 1, a thickened peracetic acid solution having a pH of about 2.7 was made by stirring for a few minutes a primary alcohol ethoxylate available from ICI under their Trademark SYNPERONIC A2 having a chain length of $C_{13}$ to $C_{15}$ and an EO number of 2 and a cocodihydroxyethylamine oxide available from Akzo under their Trademark AROMOX C12W at ambient temperature of about 22° C., the amounts of the alcohol ethoxylate and amine oxide being chosen to give concentrations of 7% w/w and 3% w/w respectively in the thickened composition. Into the surfactant pre-mix was added, with gentle stirring, an aqueous solution containing 1% peracetic acid, 7% hydrogen peroxide and 9% acetic acid. The viscosity of the composition after storage for 1 day to allow any entrapped air to escape was measured by a Brookfield viscometer, using spindle no 2 at 50 rpm as 330 cPs. The composition was stored in a polyethylene container and held at 32° C. in a laboratory storeroom. After 6 weeks, the viscosity of the composition was measured in the same way and a reading of 330 cPs was obtained. The chemical stability of the composition was measured by measuring the peracid concentration in the composition before and after the 6 weeks storage by the standard technique employing ceric sulphate/sodium iodide-sodium thiosulphate. It was found that the amount of peracid was the same at the end as at the start of the storage, indicating that no detectable amount of decomposition of the peracid had occurred.

From the results obtained in Example 1, it can be deduced that the thickening system employed therein is effective in not only thickening the soluble peracid composition, but is also capable of maintaining both physical and chemical storage stability of the composition during the expected shelf-life of a disinfectant for the domestic market.

When each component of the thickening system is employed alone, no significant thickening of the composition is observed.

EXAMPLE 2

In Example 2, the method of Example 1 was repeated, except that 7.5% of a secondary alcohol ethoxylate commercially available from Union Carbide under their Trademark TERGITOL 15-S-3 having a C15 carbon chain and an EO number of 3 was employed in place of the SYNPERONIC A2. The viscosity of the composition was 312 cPs after storage for 1 day and 312 cPs after 12 weeks storage. Its peracid content at the end of the storage period was still >85% of the starting amount.

From this example it can be deduced that the use of a secondary alcohol ethoxylate having a C15 carbon chain and an EO number of 3 gave acceptable physical and chemical storage stability.

EXAMPLE 3

In Example 3, the method of Example 2 was repeated, except that an additional 3% of a primary alcohol ethoxylate available from ICI under their Trademark SYNPERONIC A4 having a chain length of $C_{13}$ to $C_{15}$ and an EO number of 4 was also employed. This gave a composition having a viscosity of 1760 cPs after storage for 1 day.

EXAMPLE 4

In Example 4, the method of Example 1 was repeated, except employing 10.5% of SYNPERONIC A2. This gave a composition having a viscosity of 1620 cPs after storage for 1 day.

EXAMPLE 5

In Example 5, the method of Example 1 was repeated, except employing 10.5% of TERGITOL 15-S-3. This gave a composition having a viscosity of 1560 cPs after storage for 1 day.

EXAMPLE 6

In Example 6, the method of Example 2 was repeated, except that the peracetic acid solution comprised 0.086% peracetic acid, 0.7% hydrogen peroxide and 1.1% acetic acid having a pH of 2.6. The thickened composition had a pH of 3.3 and a viscosity of 860 cPs.

EXAMPLES 7 AND 8

In these Examples, the method of Example 6 was repeated, except that the pH of the peracetic acid solution was reduced to pH 2.0 and 1.6 respectively by the addition of 98% w/w sulphuric acid solution prior to the addition of the thickening system. The thickened compositions had pH's of 3.3 and 2.9, with viscosities of 540 cPs and 240 cPs, respectively.

EXAMPLES 9–16

In these Examples, the method of Example 2 was followed, except that the peracetic acid solution comprised 0.89% w/w peracetic acid, 7.7% w/w hydrogen peroxide and 10.85% w/w acetic acid. The pH of the peracetic acid solution prior to thickening was 1.9. In Example 9, this solution was employed without pH adjustment prior to the addition of the thickening system. In Examples 10, 11 and 12, the pHs of the peracetic acid solutions prior to thickening for were adjusted to 2.0, 2.1 and 2.2 respectively by the addition of 10% W/w sodium hydroxide solution, and for Examples 13, 14, 15 and 16 to pHs 2.0, 2.1, 2.2 and 2.3 respectively by the addition of 10% w/w ammonium hydroxide solution. The viscosities of the thickened compositions produced are given below:

| Example No. | 9 | 10 | 11 | 12 | 13 | 14 | 15 | 16 |
|---|---|---|---|---|---|---|---|---|
| Viscosity (cPs) | 624 | 416 | 232 | 104 | 372 | 276 | 232 | 148 |

EXAMPLES 17–20

A thickened peracetic acid composition was produced by the general method of Example 9. The thickened composition produced was divided into 4 aliquots. In Example 17, no sodium sulphate was dissolved in the composition. In Examples 18, 19 and 20, anhydrous sodium sulphate was dissolved in the compositions to give 200 mg/l, 400 mg/l and 600 mg/l of $SO_4$ respectively. The viscosities of the compositions are given below.

| Example No. | 17 | 18 | 19 | 20 |
|---|---|---|---|---|
| Viscosity (cPs) | 648 | 464 | 280 | 96 |

The results for Examples 17 to 20 demonstrated that the thickening system could be employed to thicken solutions having a varying ionic strength, but that increased ionic strength tended to reduce the viscosity achieved for a given peroxygen composition and concentration of thickening system.

EXAMPLES 21 AND 22

In these Examples, the method of Example 2 was followed, except that the surfactants employed were 9% w/w of sodium dodecylbenzenesulphonate (commercially available in the UK from Cargo Fleet Chemicals under the trade name "Caflon NAS30") for Example 21, and 9% of lauryl dimethylbetaine (commercially available in the UK from Surfachem under the trade name "Empigen BB") for Example 22. The viscosities of the compositions were 340 cPs and 44 cPs, respectively.

We claim:

1. A thickened aqueous composition comprising 0.01 to 40% w/w of a water-soluble peracid in solution together with a thickener wherein the thickener comprises:
   (a) an aliphatic alcohol ethoxylate having the formula:

$R^1R^2CH-(OCH_2CH_2)_n-OH$ in which $R^1$ and $R^2$ are hydrogen or linear or branched alkyl,
   in which n is an integer of at least 1,
   in which, when neither $R^1$ nor $R^2$ is a hydrogen atom, $R^1$ and $R^2$ have in total from 10 to 18 carbon atoms, and the number ratio of carbon atoms in $R^1$ plus $R^2$:n is in the range of from 4:1 to 7:1, and
   in which when either $R^1$ or $R^2$ is a hydrogen atom, the total number of carbon atoms is from 7 to 16 carbon atoms and the number ratio of carbon atoms in $R^1$ plus $R^2$:n is in the range of from 4:1 to 9:1; and
   (b) an amine oxide co-surfactant in an amount sufficient to increase the viscosity of the composition, said ethoxylate (a) being present in an amount of from 2.5 to 15% w/w, said co-surfactant (b) being present in an amount of from 0.1 to 5% w/w, and the weight ratio of said ethoxylate (a) to said co-surfactant (b) being from 2:1 to 20:1.

2. A composition according to claim 1 wherein, in the formula, either $R^1$ or $R^2$ is a hydrogen atom and the number ratio of carbon atoms in $R^1$ plus $R^2$:n is in the range of from 5:1 to 8:1.

3. A composition according to claim 2, wherein the total number of carbon atoms is from 9 to 16 carbon atoms.

4. A composition according to claim 1, wherein the water soluble peracid comprises peracetic acid.

5. A composition according to claim 1, or 4 wherein the pH of the thickened composition is 2.0 or more.

6. A composition according to claim 5, wherein the pH of the thickened composition is in the range of from 2.3 to 4.

7. A composition according to claim 1 or 4, wherein the weight ratio of alcohol ethoxylate (a) to co-surfactant (b) is in the range of from 4:1 to 15:1.

8. A composition according to claim 1 or 4, wherein the weight ratio of alcohol ethoxylate (a) to co-surfactant (b) is from 6:1 to 12:1.

9. A composition according to claim 1, or 4 wherein the co-surfactant (b) is selected from amine oxides comprising a C10 to C18 alkyl group.

10. A composition according to claim 9, wherein the co-surfactant (b) comprises cocodi(hydroxyethyl)amine oxide.

11. A composition according to claim 1 or 4 wherein the viscosity is greater than 30 cPs.

12. A composition according to claim 1 or 4 wherein the solution further comprises a carboxylic acid which corresponds to the peracid and wherein the total amount of peracid plus corresponding carboxylic acid in the peracid composition is less than 30% w/w.

13. A composition according to claim 12 wherein the total amount of peracid plus corresponding carboxylic acid in the peracid composition is less than 16% w/w.

14. A composition according to claim 1 or 4 wherein the concentration of peracid is from 0.05 to 5% w/w.

15. A composition according to claim 14, wherein the concentration of peracid is from 0.1 to 2% w/w.

16. A composition according to claim 1 or 4 wherein the peracid solution is substantially free from mineral acid.

17. A method for disinfecting and/or cleaning a hard surface comprising contacting the hard surface with a composition according to claim 1 or 4.

18. A process for thickening an aqueous peracid solution, containing from 0.01 to 40% w/w of a water-soluble peracid, said process comprising introducing into said solution:

(a) an aliphatic alcohol ethoxylate having the formula:

$$R^1R^2CH\text{---}(OCH_2CH_2)_n\text{---}OH$$

in which $R^1$ and $R^2$ are hydrogen or linear or branched alkyl, in which n is an integer of at least 1, in which, when neither $R^1$ nor $R^2$ is a hydrogen atom, $R^1$ and $R^2$ have in total from 10 to 18 carbon atoms, and the number ratio of carbon atoms in $R^1$ plus $R^2$:n is in the range of from 4:1 to 7:1, and in which when either $R^1$ or $R^2$ is a hydrogen atom, the total number of carbon atoms is from 7 to 16 carbon atoms and the number ratio of carbon atoms in $R^1$ plus $R^2$:n is in the range of from 4:1 to 9:1; and (b) an amine oxide co-surfactant in an amount sufficient to increase the viscosity of the compositions, said ethoxylate being present in an amount of from 2.5 to 15% w/w, said co-surfactant being present in an amount of from 0.1 to 5% w/w, and the weight ratio of said ethoxylate (a) to said co-surfactant (b) being from 2:1 to 20:1.

19. A process according to claim 18, wherein the aliphatic alcohol ethoxylate and co-surfactant are pre-mixed prior to the addition of the peracid solution.

20. A process according to claim 18, wherein, in the formula, either $R^1$ or $R^2$ is a hydrogen atom and the number ratio of carbon atoms in $R^1$ plus $R^2$:n is in the range of from 5:1 to 8:1.

21. A process according to claim 20, wherein the total number of carbon atoms is from 9 to 16 carbon atoms.

22. A process according to claim 18, wherein the water soluble peracid comprises peracetic acid.

23. A process according to claim 18 or 22, wherein the pH of the thickened composition is 2.0 or more.

24. A process according to claim 23, wherein pH of the thickened composition is in the range of from 2.3 to 4.

25. A process according to claim 18 or 22, wherein the weight ratio of hydrophobic alcohol ethoxylate (a) to co-surfactant (b) is in the range of from 4:1 to 15:1.

26. A process according to claim 18 or 22, wherein the weight ratio of hydrophobic alcohol ethoxylate (a) to co-surfactant (b) is from 6:1 to 12:1.

27. A process according to claim 18 or 22, wherein the co-surfactant (b) is selected from amine oxides comprising a C10 to C18 alkyl group.

28. A process according to claim 18 or 22, wherein the co-surfactant (b) comprises cocodi(hydroxyethyl)amine oxide.

29. A process according to claim 18 or 22, wherein the solution further comprises a carboxylic acid which corresponds to the peracid, and wherein the total amount of peracid plus corresponding carboxylic acid in the peracid composition is less than 30% w/w.

30. A process according to claim 29 wherein the total amount of peracid plus corresponding carboxylic acid in the peracid composition is less than 16% w/w.

31. A process according to claim 18 or 22, wherein the concentration of peracid is from 0.05 to 5% w/w.

32. A process according to claim 18 or 22, wherein the concentration of peracid is from 0.1 to 2% w/w.

33. A process according to claim 18 or 22, wherein the peracid solution is substantially free from mineral acid.

* * * * *